United States Patent
Anderson

(10) Patent No.: US 9,278,050 B2
(45) Date of Patent: Mar. 8, 2016

(54) DISSOLVABLE MEDICATION ADMINISTRATION BAG AND METHOD OF USING THE SAME

(71) Applicant: Trevor Anderson, Spokane, WA (US)

(72) Inventor: Trevor Anderson, Spokane, WA (US)

(*) Notice: Subject to any disclaimer, the term of this patent is extended or adjusted under 35 U.S.C. 154(b) by 0 days.

(21) Appl. No.: 14/231,456

(22) Filed: Mar. 31, 2014

(65) Prior Publication Data

US 2014/0294952 A1    Oct. 2, 2014

Related U.S. Application Data

(60) Provisional application No. 61/807,082, filed on Apr. 1, 2013.

(51) Int. Cl.
| | |
|---|---|
| *A61J 1/03* | (2006.01) |
| *A61K 9/20* | (2006.01) |
| *A61J 7/00* | (2006.01) |
| *A61K 9/00* | (2006.01) |
| *A61J 1/10* | (2006.01) |

(52) U.S. Cl.
CPC ............ *A61J 1/03* (2013.01); *A61J 7/0007* (2013.01); *A61K 9/009* (2013.01); *A61J 1/10* (2013.01)

(58) Field of Classification Search
CPC ............. A61J 1/03; A61J 1/10; A61J 7/0007; A61K 9/0009; A61K 9/20
See application file for complete search history.

(56) References Cited

U.S. PATENT DOCUMENTS

| | | | |
|---|---|---|---|
| 3,784,390 A | 1/1974 | Hijiya | |
| 5,586,732 A | 12/1996 | Yamauchi et al. | |
| 5,674,522 A * | 10/1997 | Shah et al. | 424/439 |
| 5,948,430 A | 9/1999 | Guo et al. | |
| 6,143,316 A * | 11/2000 | Hayden et al. | 424/442 |
| 7,051,963 B1 | 5/2006 | Buckley | |
| 7,090,858 B2 * | 8/2006 | Jayaraman | 424/400 |
| 7,347,394 B2 | 3/2008 | Buckley | |
| 7,491,406 B2 | 2/2009 | Leung et al. | |
| 7,637,449 B1 | 12/2009 | Leyshon | |
| 7,648,093 B2 | 1/2010 | Kruger | |
| 8,282,954 B2 | 10/2012 | Bogue et al. | |
| 2004/0247649 A1 * | 12/2004 | Pearce et al. | 424/440 |
| 2006/0073190 A1 * | 4/2006 | Carroll et al. | 424/440 |
| 2007/0297701 A1 | 12/2007 | Engel et al. | |

FOREIGN PATENT DOCUMENTS

WO    WO 2011046861 A1 *    4/2011

* cited by examiner

*Primary Examiner* — Abigail Fisher
(74) *Attorney, Agent, or Firm* — Lee & Hayes, PLLC

(57) ABSTRACT

A dissolvable medication administration bag for the safe and effective crushing and administration of medication to patients who have difficulty swallowing pills. A dissolvable medication administration bag may be constructed in accordance with a pill crusher pouch embodiment into which a pill is placed prior to being crushed and subsequently the whole of pouch and the crushed pill contents are dissolved into a liquid, e.g. a beverage, as a means of reducing health hazards associated with current pill crushing practices such as inadvertent direct contact and aerosolization with subsequent inhalation of the crushed medication.

10 Claims, 2 Drawing Sheets

DISSOLVABLE MEDICATION ADMINISTRATION BAG AND METHOD OF USING THE SAME

CROSS-REFERENCE TO RELATED APPLICATIONS

The present application claims the benefit of U.S. Provisional Patent Application No. 61/807,082 filed Apr. 1, 2013, entitled "Dissolvable Medication Administration Bag," which is incorporated herein by reference in their entirety as if fully set forth herein.

FIELD OF THE DISCLOSURE

This disclosure relates generally to the field of medication administration, and more specifically, to a dissolvable medication administration bag for the safe and effective crushing of pill form medications and subsequently dissolving thereof into a liquid, such as a beverage, thereby enabling an administration of medications to patients who have difficulty swallowing the medications in pill form.

BACKGROUND

A market currently exists for apparatuses related to the crushing of certain pill form medications for ease of administration to patients whom have difficulty swallowing medications in pill form. For example, many patients struggle to swallow medications in pill form due to the size and shape of common pills and thus medical staff may resort to crushing the pill and mixing the crushed medication with food or liquid to consume it. Moreover, some patients are completely unable to swallow and rely exclusively on a feeding tube. While the terms "pill," "capsule," and "tablet" may have distinct meanings and one skilled in the art may be able to recognize the differences, as used herein the term "pill" is intended to include all three terms and any reasonable equivalents currently known in the field or developed hereafter. Because of this recognized need, a variety of pill crushing devices as well as pill crusher pouches are well-known in the art.

Generally, in order to administer a crushed pill the following steps are performed. First, the pill is placed inside a pill crusher pouch. Second, the pill crusher pouch, with the pill inside, is placed inside a crushing region of a pill crusher device Third, the pill crusher device then exerts a force on the surface of the pouch thereby crushing its contents. Fourth, the now crushed medication is poured from the pill crusher pouch into a beverage which the particles are either dissolved into or suspended within. Finally, the medication is administered by the patient consuming the beverage. There are, however, recognized problems associated with the current state of pill crusher pouches. For example, it is impracticable to extract all of the medication from current pill crusher pouches because particles tend to accumulate in the corners of the pouch and particles also cling to or embed into the pouch material itself. Consequently, the appropriate dosage of medication is not administered. Attempts have been made to solve this problem; however, so far as Applicant is aware no such attempt completely eliminates the problem.

U.S. Pat. No. 7,347,394 to Buckley, dated Mar. 25, 2008, and fully incorporated by reference herein, discloses a pill crusher pouch wherein the closed bottom of the pouch comprises a cup like seal, thus providing a pouch with a cornerless interior to facilitate easier pouring of the pulverized medication from the interior of the pouch. A main design feature of the Buckley pill crusher pouch is the elimination of the sharp pouch corners found in previous pill crusher pouches which is intended to eliminate the accumulation of crushed medication at the corners in order to administer a more complete dose of the crushed medication.

U.S. Pat. No. 7,637,449 to Leyshon et al., dated Dec. 29, 2009, and fully incorporated by reference herein, discloses a pill crusher pouch having a slanted bottom adapted to direct crushed medication toward a focal point along the bottom and at least one perforation line intersecting the bottom slightly above the focal point. In order to dispense the crushed medication, the portion of the pill crusher pouch below the perforation is torn to create a funnel-like structure which guides the crushed medication to the desired location.

While many pill crusher pouches, such as those described supra, comprise geometrical optimizations as a means of facilitating more complete extraction of a crushed medication, an amount of crushed particle may become embedded in or even cling to the flat inner surfaces of the pouch. Therefore, so long as a crushed medication is poured from a pill crusher pouch it cannot be guaranteed that one hundred percent of the medication will be extracted and administered. In this regard, there is a need for a new and improved pill crusher pouch that allows the whole of a crushed pill to be consumed by a patient.

In addition to improper dosage administration, the crushing of some pills creates particles which are small enough to be carried through the air, an effect known as aerosolization. Aerosolized particles can then be inhaled through the lungs of caregivers or patients or both. With certain medications, aerosolization and inhalation has seriously adverse health effects. The problem of inadvertent aerosolization is exacerbated when a drug is poured from a pill crushing bag, e.g. into a food or liquid prior to administration. E.g., tamoxifen is a cytotoxic drug routinely used in the management of breast cancer which can be dangerous to caregivers if inhaled. Anthony James et al., *The legal and clinical implications of crushing tablet medication*, Nursing Times, Vol. 100, no. 50 (Dec. 14, 2004), p. 28. Moreover, some medications require special handling considerations by patients and caregivers because of their potentially deleterious effects to those who come into inadvertent contact with the drug. E.g., mycophenolate (CellCept®) is an immunosuppressant used for organ transplant patients which acts as a carcinogen (cancer-causing agent) if it comes into contact with the skin; and finasteride (Proscar®, also marketed as Propecia®) is a drug used to treat prostate enlargement and male pattern baldness which has teratogenic properties and should not be touched by women of childbearing age. Donna Gill, DNP et al., *Crushing and Splitting Medications Unrecognized Hazards*, Journal of Gerontological Nursing, Vol. 38, no. 1 (January 2012), pp. 8-12. Many medications which can have deleterious effects if inadvertently contacted are manufactured in pill form with a protective coating to prevent contact with the medication during handling and, ultimately, to reduce the risk of harming those handling the drug. Crushing such pills obviously destroys their protective coatings. The problems associated with inadvertent contact and aeresolization have been recognized by health organizations including the National Institute for Occupational Safety and Health (NIOSH) and, in regard to these problems, there is a need for a new and improved pill crusher pouch that prevents both the aerosolization of the crushed medication as well as other types of inadvertent contact that may result from the crushing and administering a medication originally in pill form.

Even beyond the problems of inhalation after aerosolization and other inadvertent contact with medications, other problems associated with the crushing of certain medications remain. In fact, many pills have specific properties designed into the pill structure that go beyond simply the type of medication contained therein, and crushing such pills often destroys these desirable properties. For example, extended release medications, i.e. pills specifically designed to dissolve a medication over time in order for it to be released slower and steadier into the bloodstream while having the advantage of being taken at less frequent intervals than immediate-release formulations of the same drug, often contain a higher dosage than their immediate release counterparts. If these drugs are crushed they lose their ability to slow the rate at which the medication is absorbed into the patient's bloodstream. Therefore, the improper crushing of an extended release medication results in a higher dosage of medication being administered and can have deleterious consequences because the pharmacokinetic and pharmacodynamic properties will be unpredictable and inconsistent. Categories of extended release (ER) medication (and their associated prefix or suffix) which lose their desirable properties if crushed include continuous release (CC), controlled dose (CD), controlled release (CR), long acting (LA), slow action (Retard), slow release (Slo-), sustained action (SA), and sustained release (SR). In addition to extended release medications, the following should not be crushed prior to administration: enteric or protected coating medications designed to dissolve in the intestines; medications formulated for sublingual (under the tongue) or buccal (between the cheek and gums) administration; and those designed to exert a local effect in the mouth. In regard to the aforementioned problems, there is a need for a medication administration bag that mitigates the risk of health care professionals crushing medications for ease of patient consumption when said medications are of a type unsuitable for being crushed.

Accordingly, this application discloses a dissolvable medication administration bag that meets the needs recognized supra. The dissolvable medication administration bag may be utilized in the form of a dissolvable pill crusher pouch that allows for the whole of a crushed pill to be consumed by the patient and that also prevents inadvertent contact with the crushed medication, i.e. both direct contact and inhalation after aerosolization are prevented. In such an embodiment, after a medication has been crushed inside the pouch the entirety of the pouch and its contents are placed in a liquid into which both the pouch and its contents fully dissolve. Additionally, the dissolvable medication administration bag may be utilized in the form of a pre-packaged dissolvable medicine dosage administration bag that allows for health care professionals to dissolve certain allowable medications into a beverage or the nutritional contents of a feeding tube for ease of administration while mitigating the risk of destroying desirable properties specifically designed into the pill structure. In such an embodiment, the medication may be pre-measured and pre-packaged in a controlled environment, e.g. in a manufacturing facility or in a pharmacy by a licensed pharmacist, so that there is no confusion at the place of administration as to which medications may be dissolved into a beverage or feeding tube supply for ease of administration.

All references cited herein are incorporated herein by reference in their entireties.

SUMMARY

A dissolvable medication administration bag for the safe and effective crushing and administration of certain medications to patients who have difficulty swallowing the medications in pill form is disclosed herein.

In some embodiments, the dissolvable medication administration bag is constructed in accordance with a pill crusher pouch embodiment wherein a pill is placed prior to being crushed and subsequently the whole of the pouch and the crushed pill contents are submerged under and dissolved into a liquid, e.g. a beverage of the patient's choice, as a means of reducing health hazards associated with current pill crushing practices such as inadvertent direct contact and aerosolization and subsequent inhalation of the crushed medication. Such an embodiment may include a pouch having one or more walls forming an interior region for containing a pill during a pill crushing operation, wherein the pouch having one or more walls forming an interior region is at least partially constructed of a material which is at least partially soluble within one or more types of fluid, e.g. a dissolvable and edible material, and whereby a pill placed within the interior region of the pouch is capable of being crushed and subsequently dissolved and/or suspended into a liquid by submerging the pouch along with crushed pill contents into the liquid, wherein the material which is at least partially soluble within one or more types of fluid dissolves.

In other embodiments, the dissolvable medication administration bag is constructed in accordance with a pre-packaged medicine dosage administration bag embodiment wherein the whole of the pre-packaged bag and its powdered or liquid form medication contents are submerged under and dissolved into a liquid with no need for crushing.

The following embodiments and descriptions are for illustrative purposes only and are not intended to limit the scope of the dissolvable medication administration bag and methods of using the same. Other aspects and advantages of the present disclosure will become apparent from the following detailed description.

BRIEF DESCRIPTION OF THE DRAWINGS

Embodiments of the present disclosure are described in detail below with reference to the following drawings. These and other features, aspects, and advantages of the present disclosure will become better understood with regard to the following description, appended claims, and accompanying drawings. The drawings described herein are for illustrative purposes only of selected embodiments and not all possible implementations and are not intended to limit the scope of the present disclosure. Also, the drawings included herein are considered by the applicant to be informal.

DETAILED DESCRIPTION

A dissolvable medication administration bag and methods of using the same for the safe and effective crushing and administration of certain medications to patients who have difficulty swallowing the medications in pill form is disclosed herein. Specific details of certain embodiments are set forth in the following description and in FIGS. 1-3 to provide a thorough understanding of such embodiments. The present dissolvable medication administration bag and methods of using the same may have additional embodiments, may be practiced without one or more of the details described for any particular described embodiment, or may have any detail described for one particular embodiment practiced with any other detail described for another embodiment.

Figure 1:
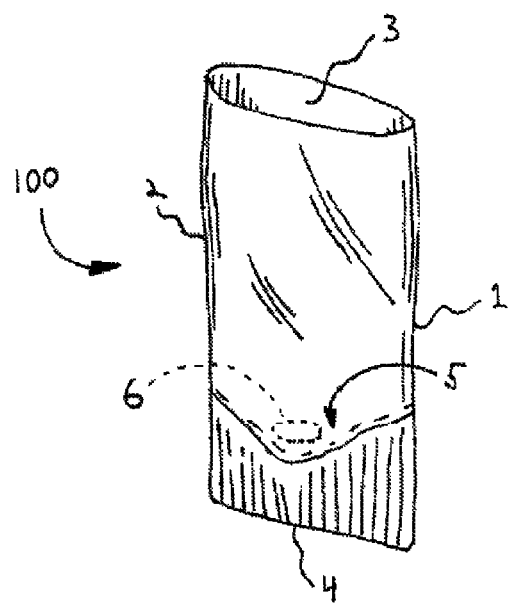
FIGS. 1-2 illustrate front elevation views of the dissolvable medication administration bag constructed in accordance with various pill crusher pouch embodiments as disclosed herein.

FIG. 1 is a front elevation view of the dissolvable medication administration bag constructed in accordance with a pill crusher pouch embodiment as disclosed herein. In some embodiments, the dissolvable pill crusher pouch 100 forms an interior region, i.e. the region lying generally within one or more walls of the dissolvable pill crusher pouch. In some embodiments, the dissolvable pill crusher pouch may further include one or more elements including a first side edge 1, a second side edge 2, an open top end 3, and a closed bottom end 4, wherein the pill crusher pouch 100 is constructed of a material which is at least partially soluble within one or more types of fluid, e.g. a dissolvable and edible material such as pullulan. The following embodiments and descriptions are for illustrative purposes only and are not intended to limit the scope of the dissolvable medication administration bag. As used herein, the term dissolve includes but is not limited to completely mixing with and becoming a part of a liquid but also includes breaking up and dispersing and/or to disintegrate.

Still referring to FIG. 1, the dissolvable pill crusher pouch 100 affords several advantages over prior art pill crusher pouches. The pouch 100 allows for the whole of a crushed medication to be dissolved into a beverage and, therefore, to be consumed by the intended recipient because, unlike existing pill crusher pouches, the dissolvable pill crusher pouch 100 disclosed herein does not require the pouring of the crushed medication from the pouch. Rather the whole of the pouch 100 and its crushed contents are dissolved into a beverage ensuring that the entire dosage of medication is administered to the patient. Thus, in contrast to existing pill crusher pouches, the dissolvable pill crusher pouch disclosed herein is non-reliant on geometrical optimization of the pouch to deliver the entire dose of a crushed medication. An additional benefit of the dissolvable pill crusher pouch 100 is that by eliminating the need to pour the crushed medication from the pouch, severe health hazards associated with aerosolization of crushed medication are reduced or eliminated while also speeding the work flow process for health care workers.

In some embodiments, the dissolvable pill crusher pouch 100 is formed to comprise, within the interior region of the pouch, at least one sloped region contiguous with and leading to a bottommost inner region, indicated generally at 5, such that a content of the pouch, e.g. a pill 6, will tend toward the bottommost inner region 5 of the pouch, the location of which is chosen based on the optimal crushing zone of a particular pill crushing device, when the pouch is in an upright orientation. As used herein, the term "upright orientation" refers to the orientation depicted in each of FIGS. 1-2, e.g. with the open top ends 3 and 10 oriented closer to the top of the drawing sheet than the corresponding closed bottom ends 4 and 11 of each embodiment. In order to completely mitigate the risk of aerosolization, it is contemplated that the pouch 100 may be either folded or clamped closed at or near the top open end 3 subsequent to the pill 6 being inserted into the pouch and prior to the pill 6 being crushed within the pouch. For example, standard hemostatic clamps are widely available in medical facilities and could easily be used to both clamp the pouch 100 closed to prevent aerosolization as well as to place the pouch in a liquid. Moreover, assuming it is sterilized prior to use, the chosen clamping mechanism could also be used to stir the liquid as a means of facilitating rapid dissolving of the pouch and crushed medication.

Figure 2:
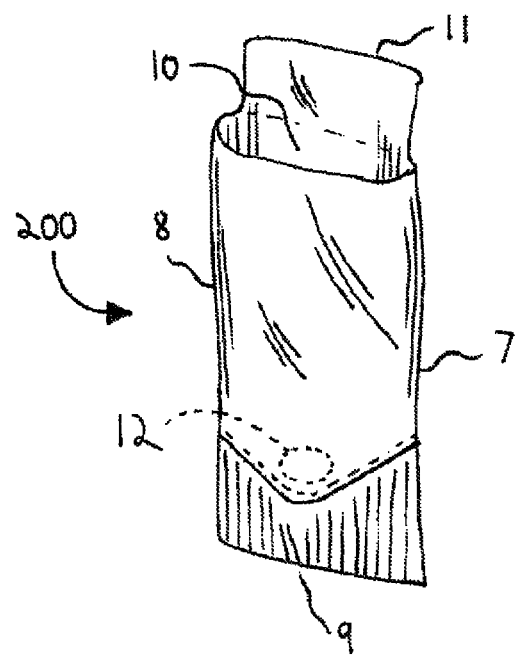

Referring now to FIG. 2, a front elevation view of the dissolvable medication administration bag constructed in accordance with a preferred pill crusher pouch embodiment as disclosed herein is illustrated. In some embodiments, the dissolvable pill crusher pouch 200 may include one or more elements including a first side edge 7, a second side edge 8, a closed bottom end 9, and an open top end 10 which further comprised a flap 11. As used herein the term flap refers to an extended part for foldably forming a closure of the pouch. As with other embodiments, the pill crusher pouch 200 is constructed of a material which is at least partially soluble within one or more types of fluid, e.g. a dissolvable and edible material. In some of such embodiments, the flap 11 is intended to be folded and inserted into the open top end 10 to create at least a partial seal of the open top end 10 and, more specifically, to reduce the occurrence of aerosolization and inadvertent drug contact. In other such embodiments, the flap 11 comprises an adhesive at a predetermined location, e.g. on the front and upper portion of the flap as oriented in FIG. 2, that allows for the flap to be folded over the top end 10 or tucked into the top end 10 such that the adhesive creates a more robust seal than could otherwise be achieved.

It should be appreciated that while only certain configurations have been disclosed herein, many other configurations may be utilized to reduce undesirable effects of use, mainly aerosolization, and that such configurations are intended to be within the scope of the dissolvable medication administration bag disclosed herein.

Figure 3:
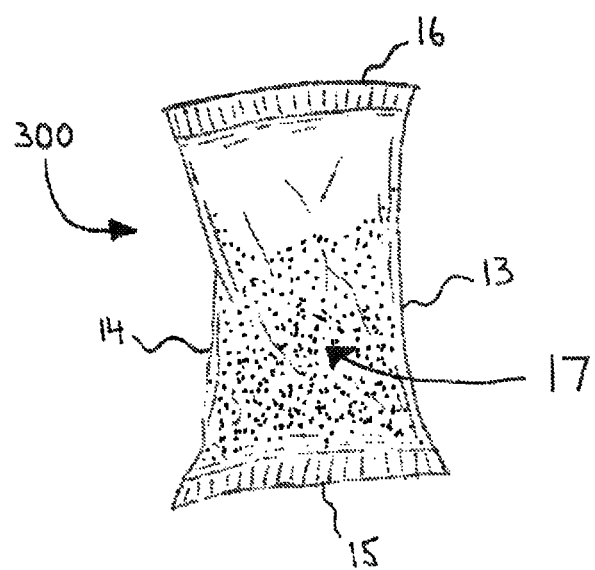
FIG. 3 is a front elevation view of the dissolvable medication administration bag constructed in accordance with a pre-packaged medicine dosage administration bag embodiment as disclosed herein.

Referring now to FIG. 3, a front elevation view of the dissolvable medication administration bag constructed in accordance with a pre-packaged medicine dosage administration bag embodiment as disclosed herein is illustrated. In some embodiments, the dissolvable pre-packaged medicine dosage administration bag 300 may include one or more elements including a first side edge 13, a second side edge 14, a first closed end 15, and a second closed end 16, wherein the combination of edges form an enclosed inner region 17 of the pouch in which a dosage of powdered medication is enclosed. Because the medication is pre-measured and pre-packaged in powdered form there is no need for crushing the medication and, therefore, this and similar embodiments mitigate the risks discussed in the background section, and other risks, which are associated with health care professionals crushing medications for ease of patient consumption, e.g. not only aerosolization but also crushing medications with extended release properties. As with other embodiments, the pill crusher pouch 300 is constructed of a material which is at least partially soluble within one or more types of fluid, e.g. a dissolvable and edible material. Thus, similar to embodiments 100 and 200, in order to administer the medication the pre-packaged bag 300 is simply combined with a liquid, e.g. a beverage of the patients choice, in which the bag and its contents are fully dissolved prior to patient consumption. It should be appreciated that the contents of the dissolvable pre-packaged medicine dosage administration bag 300 is not limited to medication in powdered form, i.e. other forms of medication may also be used such as, for example, liquid form medications. However, for many types of medications the solid form of the medication is more stable than its liquid form counterpart and, therefore, the solid forms of certain medications are preferred due to characteristics such as longer shelf life. Moreover, liquid medications are inherently heavier than the solid form of the same medication and, therefore, shipping costs will be more for embodiments with liquid medication contents.

In some embodiments, the pre-packaged medicine dosage administration bag comprises compartmentalized components, e.g. one compartment may contain the drug while another compartment contains a flavoring agent. In these instances, caregivers may provide the patient with a flavorful beverage wherein the added flavor masks any unwanted taste of the drug as is done today but without the additional step of ordering or preparing the flavored beverage. For example, today caregivers might order a juice as a step in administering a crushed pill whereas this embodiment would eliminate this step and streamline the caregiver's workflow.

Despite that the pre-packaged medicine dosage administration bag disclosed herein is a preferred pre-packaged embodiment because no crushing step is required by caregivers, it is contemplated that the cost associated with manufacturing both a pill form and a pre-packaged medicine dosage administration bag of the same drug may prove to be cost prohibitive due to a variety of factors, such as for example additional tooling requirements. Therefore, it is contemplated by inventor that various pill crusher pouch embodiments may and will be used to pre-package drug dosages, e.g. a pharmacist may place a specific pill within a dissolvable pill crusher pouch and label it for later crushing and administration. Such a process would help mitigate the risk of crushing pills which are unsuited for crushing, e.g. time release pills, because the individual placing the pill into the pill crusher pouch would be more highly trained in which pills are acceptably crushed than general hospital staff administering the pills.

Now that various embodiments of the dissolvable medication administration bag have been described in terms of their geometrical characteristics, it may be beneficial now to describe materials which are at least partially dissolvable within one or more types of fluid. For example, materials which are both dissolvable and edible may be suitable for use in constructing certain embodiments of the present disclosure.

Many types of dissolvable and edible films currently exist on the market. E.g., the household oral hygiene company Listerine® manufactures and sells breath strips in portable sized Pocketpaks®. The breath strips are made from an edible film that dissolves instantly when it becomes exposed to water. Listerine® breath strips are made with a polysaccharide polymer known as pullulan. Pullulan is an edible and mostly tasteless polymer which is chiefly used in the manufacture of edible films. U.S. Pat. No. 7,491,406 B2 to Leung et al., dated Feb. 17, 2009, and fully incorporated by reference herein, discloses pullulan based edible films which further contain antimicrobial effective amounts of the essential oils thymol, methyl salicylate, eucalyptol, and menthol. It has been found that such a film has suitable mechanical properties for use as the dissolvable and edible material and that the film dissolves rapidly in warm water. Thus, such a pullulan based film could be used to the exclusion of the essential oils or, assuming the essential oils do not effect a given medication, the film could contain the oils also.

The versatility of pullulan based products is further described in expired U.S. Pat. No. 3,784,390 to Hijiya et al., dated Jan. 8, 1974, and fully incorporated by reference herein, which discloses pullulan products and their ability to be shaped through compression molding or extruding the material at elevated temperatures. Pullulan films have many desirable mechanical properties such as a tensile strength on the order of magnitude of the common packaging material cellophane (regenerated cellulose), or even higher if desired, and that even very thin pullulan films are nearly impermeable to atmospheric oxygen. Moreover, pullulan films are soluble even in cold water. Accordingly, pullulan films may be used as the dissolvable and edible material in at least some embodiments of the dissolvable medication administration bag disclosed herein, including both pill crusher pouch embodiments and pre-packaged medicine dosage administration bag embodiments.

Other compositions which may be suitable for use as the dissolvable and edible material in various embodiments are disclosed in: U.S. Pat. No. 8,282,954 to Bogue et al., dated Oct. 9, 2012, and fully incorporated by reference herein; and U.S. Pat. No. 5,948,430 to Guo et al., dated Sep. 7, 1999, and fully incorporated by reference herein.

Another edible film which may be suitable for use as the dissolvable and edible material is manufactured by Monosol® LLC (www.monosol.com) under the product name Vivos™ edible delivery Systems™ which is currently used to make pre-portioned pouches for the convenient delivery and portioning of food products.

The specific choice of the material which is at least partially dissolvable in one or more types of fluid depends, at least partially, on the mechanical properties of the pills intended to be crushed and, more specifically, the hardness of the pills intended to be crushed. In order to prevent the occurrence of tearing of the pill crusher pouch due to the pressure generated between the pill and the anvil of the pill crusher device, the strength of the edible and dissolvable material must be increased as the hardness of the pills intended to be crushed increases. The hardness, and other mechanical properties of pills such as crushing strength, can vary greatly. Hardness is typically measured using one of either a Monsanto Hardness Tester or a Stokes Hardness Tester with units of measurement of kg per cubic centimeter. Oral pills normally range in hardness from 4-10 kg per cubic centimeter; however, some pills such as sustained release pills or enteric coated pills may be much harder, e.g. upwards of 20 kg per cubic centimeter. It has been found that the pullulan based edible film marketed and sold as Listerine® Pocketpaks® Breath Strips has sufficient mechanical properties in that a variety of pills can be crushed between one or more layers of the film. Moreover, the film has been found to quickly dissolve in warm water which is another desirable characteristic of the material to be selected. Because any amount of tear through of the dissolvable pill crusher pouch may result in one or more of inadvertent drug contact and loss of medication dosage, it may be desirable to provide a sleeve component for the dissolvable pill crusher pouch 100 or 200 to be placed within prior to crushing and from which the pouch 100 or 200, along with its contents, may be poured into a liquid from.

In some embodiments, the material which is at least partially soluble within one or more types of fluid is not necessarily edible and is intended to be used in administering medication non-orally, e.g. intravenously via an intravenous line containing a saline solution, a chemotherapy solution, or any other suitable intravenous solution. In such embodiments, the material which is at least partially soluble within one or more types of fluid is at least partially soluble within the intended intravenous solution.

A method of administering a medication is further disclosed herein, the method comprising the steps of providing a medication administration apparatus containing at least one medication, the medication administration apparatus being at least partially soluble within one or more types of liquid, and placing the medication administration apparatus containing at least one medication in contact with the one or more types of liquid, thereby causing the medication administration apparatus to at least partially dissolve into the one or more types of fluid such that the at least one medication at least partially dissolves into and/or at least partially becomes suspended within the one or more types of fluid. In some embodiments, the one or more types of fluids is a beverage of a patient's choice. In some embodiments, the one or more types of fluids is an solution intended for intravenous administration to a patient. The step of providing a medication administration apparatus containing at least one medication may include providing any one of the aforementioned embodiments 100, 200, or 300 or any other suitable medication administration apparatus.

In some embodiments of the method, the step of providing a medication administration apparatus containing at least one medication, the medication administration apparatus being at least partially soluble within one or more types of liquid further comprises the steps of: placing a pill into an interior region of the medication administration apparatus; and crushing the pill by applying force to one or more external surfaces of the medication administration apparatus. For example, a nurse practitioner or physician may place a pill within a pill crusher pouch in accordance with 100 or 200 disclosed herein and place the pouch and pill contents within a standard pill crusher device (many are well known in the art) and then operate the standard pill crusher device to crush the pill contents.

It should be appreciated that while only certain materials which are at least partially soluble within one or more types of fluids, e.g. certain dissolvable and edible materials, have been disclosed herein, any suitable materials which are at least partially soluble within one or more types of fluids are intended to be within the scope of the dissolvable medication administration bag disclosed. Accordingly, other types of materials which are at least partially soluble within one or more types of fluids, whether currently known in the art or subsequently developed, may also be used so long as such film is suitable for the intended purpose.

While preferred and alternate embodiments have been illustrated and described, as noted above, many changes can be made without departing from the spirit and scope of the dissolvable medication administration bag. Accordingly, the scope of the dissolvable medication administration bag is not limited by the disclosure of these preferred and alternate embodiments. Instead, the scope of the dissolvable medication administration bag should be determined entirely by reference to the claims. Insofar as the description above and the accompanying drawing disclose any additional subject matter that is not within the scope of the claims below, the inventions are not dedicated to the public and Applicant hereby reserves the right to file one or more applications to claim such additional inventions.

What is claimed is:

1. A method of administering a medication, the method comprising the steps of:
   providing a medication administration pouch that is at least partially soluble within one or more types of beverages;
   placing a pill into an interior region of the medication administration pouch;
   crushing the pill by applying force to one or more external surfaces of the medication administration pouch, the crushing resulting in crushed pill contents contained within the interior region of the medication administration pouch;
   placing both of the medication administration pouch and the crushed pill contents contained within the medication administration pouch in contact with a particular beverage of the one or more types of beverages, wherein the placing causes the medication administration pouch to at least partially dissolve into the particular beverage thereby releasing the crushed pill contents into the particular beverage.

2. The method of administering a medication of claim 1, further comprising the step of:
   subsequent to the placing both of the medication administration pouch and the crushed pill contents contained within the medication administration pouch in contact with a particular beverage, orally administering the crushed pill contents to a patient by enabling the patient to orally consume the particular beverage, wherein the crushed pill contents are at least partially dissolved into the particular beverage or at least partially suspended within the particular beverage.

3. The method of administering a medication of claim 1, further comprising the step of:
   subsequent to the placing both of the medication administration pouch and the crushed pill contents contained within the medication administration pouch in contact with a particular beverage, administering the crushed pill contents to a patient via a feeding tube.

4. The method of administering a medication of claim 1, wherein the crushing comprises placing the medication administration pouch and the pill that is within the interior region into a crushing region of a pill crusher device and, subsequently, operating the pill crusher device.

5. The method of administering a medication of claim 4, wherein the interior region of the medication administration pouch comprises at least one sloped region that is contiguous with a bottommost inner region, the sloped region configured to bias the pill toward the bottommost inner region when the pouch is in an upright position.

6. The method of administering a medication of claim 1, wherein the medication administration pouch comprises:
   at least an open top end for receiving the pill into the interior region; and
   at least a closed bottom end for retaining the pill within the interior region.

7. The method of administering a medication of claim 6, further comprising the step of:
   folding a flap portion of the medication administration pouch into the at least the open top end, the folding at least partially sealing at least one of the pill or the crushed pill contents within the interior region, wherein the flap portion extends upward from the at least one open top end.

8. The method of administering a medication of claim 6, further comprising the step of:
   folding a flap portion of the medication administration pouch over the at least the open top end; and
   adhering the flap portion onto an exterior surface of the medication administration pouch.

9. The method of administering a medication of claim 6, further comprising the step of:
   clamping the at least the open top end closed.

10. The method of administering a medication of claim 6, wherein the medication administration pouch is at least partially constructed of at least one of the water soluble polymers selected from the group consisting of pullulan, hydroxypropylmethyl cellulose, hydroxyethyl cellulose, hydroxypropyl cellulose, polyvinyl pyrrolidone, carboxymethyl cellulose, polyvinyl alcohol, sodium aginate, polyethylene oxide, polyethylene glycol, xanthan gum, tragacanth gum, guar gum, acacia gum, arabic gum, polyacrylic acid, methylmethacrylate copolymer, carboxyvinyl copolymers, starch, gelatin, methylcellulose, and hypromellose.

* * * * *